United States Patent
Schneider et al.

(10) Patent No.: US 10,106,744 B2
(45) Date of Patent: Oct. 23, 2018

(54) MIXTURES OF DIALKYLPHOSPHINIC ACIDS AND ALKYLPHOSPHINIC ACIDS, A PROCESS FOR PREPARATION THEREOF AND USE THEREOF

(71) Applicant: CLARIANT FINANCE (BVI) LIMITED, Tortola (VG)

(72) Inventors: Fabian Schneider, Cologne (DE); Frank Osterod, Cologne (DE); Harald Bauer, Kerpen (DE); Martin Sicken, Cologne (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/364,895

(22) PCT Filed: Dec. 8, 2012

(86) PCT No.: PCT/EP2012/005079
§ 371 (c)(1),
(2) Date: Jun. 12, 2014

(87) PCT Pub. No.: WO2013/087180
PCT Pub. Date: Jun. 20, 2013

(65) Prior Publication Data
US 2014/0309340 A1    Oct. 16, 2014

(30) Foreign Application Priority Data
Dec. 16, 2011  (DE) .................. 10 2011 121 591

(51) Int. Cl.
| C07F 9/30 | (2006.01) |
| C07F 9/38 | (2006.01) |
| C08K 5/5313 | (2006.01) |
| C08K 5/5317 | (2006.01) |
| C09K 21/12 | (2006.01) |

(52) U.S. Cl.
CPC .............. C09K 21/12 (2013.01); C07F 9/301 (2013.01); C07F 9/3808 (2013.01); C08K 5/5313 (2013.01); C08K 5/5317 (2013.01)

(58) Field of Classification Search
CPC ........ C07F 9/38; C07F 9/3803; C07F 9/3826; C07F 9/30; C07F 9/301; C07F 9/302
See application file for complete search history.

(56) References Cited

U.S. PATENT DOCUMENTS

| 7,420,007 | B2 | 9/2008 | Bauer et al. | |
| 7,635,785 | B2 * | 12/2009 | Bauer | ................ 562/8 |
| 8,293,938 | B2 | 10/2012 | Hill et al. | |
| 2009/0054675 | A1 * | 2/2009 | Yao | .......... C07F 9/301 558/87 |
| 2009/0165598 | A1 | 7/2009 | Zhou et al. | |
| 2014/0309339 | A1 | 10/2014 | Schneider et al. | |
| 2014/0329933 | A1 | 11/2014 | Schneider et al. | |
| 2014/0336325 | A1 | 11/2014 | Bauer et al. | |
| 2014/0350149 | A1 | 11/2014 | Schneider et al. | |
| 2014/0371361 | A1 | 12/2014 | Bauer et al. | |
| 2015/0005421 | A1 | 1/2015 | Schneider et al. | |
| 2015/0005427 | A1 | 1/2015 | Bauer et al. | |
| 2015/0018464 | A1 | 1/2015 | Bauer et al. | |
| 2015/0299419 | A1 | 10/2015 | Bauer et al. | |

FOREIGN PATENT DOCUMENTS

| EP | 1 544 206 | 6/2005 |
| EP | 1 544 205 | 6/2008 |
| EP | 2 178 891 | 4/2010 |

(Continued)

OTHER PUBLICATIONS

Machine Translation of WO2006/090751A1. Aug. 31, 2006.*
Huber Acquires Safire Halogen-Free Fire Retardant Technology. Huber Engineered Materials. http://www.hubermaterials.com/blog/2015/06/huber-acquires-safire-halogen-free-fire-retardant-technology/. As viewed on Mar. 14, 2017.*
PCT international Search Report for PCT/EP2012/005079, dated Mar. 18, 2013.
PCT International Preliminary Report on Patentability for PCT/EP2012/005079, dated Jun. 17, 2014.

(Continued)

Primary Examiner — Stephen E Rieth
(74) Attorney, Agent, or Firm — Anthony A. Bisulca

(57) ABSTRACT

The invention relates to mixtures of at least one dialkylphosphinic acid of the formula (I)

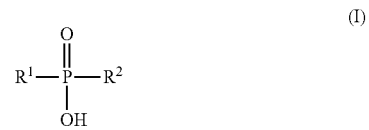

in which
$R^1$, $R^2$ are the same or different and are each independently $C_1$-$C_{18}$-alkyl, $C_2$-$C_{18}$-alkenyl, $C_6$-$C_{18}$-aryl, $C_7$-$C_{18}$-alkylaryl,
with at least one alkylphosphonic acid of the formula (II)

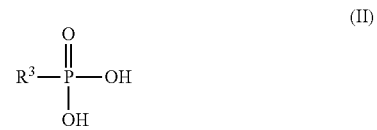

in which
$R^3$ is $C_1$-$C_{18}$-alkyl, $C_2$-$C_{18}$-alkenyl, $C_6$-$C_{18}$-aryl or $C_7$-$C_{18}$-alkylaryl;
to a process for preparation thereof and to the use thereof.

4 Claims, No Drawings

(56) References Cited

FOREIGN PATENT DOCUMENTS

WO     WO 2005/105818     11/2005
WO     WO 2006090751 A1 *   8/2006  .......... C08K 5/5313

OTHER PUBLICATIONS

Chemical Abstracts Service, Columbus, Ohio, Tsikalova, M.V. et al.: "Alkylation of white phosphorus by organocobalt (III) complexes" XP002691915, Jan. 1, 1989.
Litthauer: "Rx-ID: 5813007", XP002691916, accession No. 5813007. Chemische Berichte, vol. 22, pp. 2144-2147, Jan. 1, 1889.
Andreev et al. "Rx-ID: 4163921", XP002691917, accession No. 4163921. J. Gen. Chem., vol. 52, No. 7, pp. 1530-1537, Jan. 1, 1982.
Trofimov et al. "Rx-ID: 10418003", XP002591918, accession No. 10418003. Russian Journal of General Chemistry, vol. 75, No. 5, pp. 684-688, Jan. 1, 2005.
Petit et al. "Rx-ID: 31514043", XP002691919, accession No. 31514043. Advanced Synthesis and Catalysis, vol. 353, No. 11-12, pp. 1883-1886, Aug. 10, 2011.

\* cited by examiner

MIXTURES OF DIALKYLPHOSPHINIC ACIDS AND ALKYLPHOSPHINIC ACIDS, A PROCESS FOR PREPARATION THEREOF AND USE THEREOF

The present invention relates to mixtures of at least one dialkylphosphinic acid and at least one alkylphosphonic acid, and to a process for preparation and use thereof.

In the production of printed circuit boards, which are being used to an increasing degree in various devices, for example computers, cameras, cellphones, LCD and TFT screens and other electronic devices, different materials, especially polymers, are being used. These include particularly thermosets, glass fiber-reinforced thermosets and thermoplastics. Owing to their good properties, epoxy resins are used particularly frequently.

According to the relevant standards (IPC-4101, Specification for Base Materials for Rigid and Multilayer Printed Boards), these printed circuit boards must be rendered flame-retardant.

The thermal expansion of printed circuit boards in the course of production thereof is a problem. The conditions of electronics manufacture for printed circuit boards require that printed circuit boards withstand high thermal stresses without damage or deformation. The application of conductor tracks (lead-free soldering) to printed circuit boards is effected at temperatures up to about 260° C.

It is therefore important that printed circuit boards do not warp under thermal stress and the products remain dimensionally stable.

Thermal expansion is significant particularly even in the case of prepregs (short form of "preimpregnated fibers") and laminates, since these constitute the initial forms or precursors of printed circuit boards.

It is thus important to minimize the thermal expansion of test specimens in order to obtain a good, dimensionally stable product (finished printed circuit board).

It is therefore an object of the present invention to modify polymers for prepregs, printed circuit boards and laminates such that they are subject only to very low thermal expansion—if any at all—and dimensional stability is fulfilled.

This object is achieved by mixtures of at least one dialkylphosphinic acid of the formula (I)

(I)

in which
$R^1$, $R^2$ are the same or different and are each independently $C_1$-$C_{18}$-alkyl, $C_2$-$C_{18}$-alkenyl, $C_6$-$C_{18}$-aryl, $C_7$-$C_{18}$-alkylaryl, with at least one alkylphosphonic acid of the formula (II)

(II)

in which
$R^3$ is $C_1$-$C_{18}$-alkyl, $C_2$-$C_{18}$-alkenyl, $C_6$-$C_{18}$-aryl or $C_7$-$C_{18}$-alkylaryl.

Preferably, $R^1$ and $R^2$ are the same or different and are each methyl, ethyl, n-propyl, isopropyl, n-butyl, isobutyl, tert-butyl, n-pentyl, isopentyl, n-hexyl, isohexyl and/or phenyl; $R^3$ is [independently of $R^1$ and $R^2$]methyl, ethyl, n-propyl, isopropyl, n-butyl, isobutyl, tert-butyl, n-pentyl, isopentyl, n-hexyl, isohexyl and/or phenyl.

The mixtures preferably comprise 0.1 to 99.9% by weight of dialkylphosphinic acid of the formula (I) and 99.9 to 0.1% by weight of alkylphosphonic acid of the formula (II).

The mixtures more preferably comprise 40 to 99.9% by weight of dialkylphosphinic acid of the formula (I) and 60 to 0.1% by weight of alkylphosphonic acid of the formula (II).

More particularly, the mixtures comprise 60 to 99.9% by weight of dialkylphosphinic acid of the formula (I) and 40 to 0.1% by weight of alkylphosphonic acid of the formula (II).

The mixtures preferably also comprise 80 to 99.9% by weight of dialkylphosphinic acid of the formula (I) and 20 to 0.1% by weight of alkylphosphonic acid of the formula (II).

Preference is likewise given to mixtures comprising 90 to 99.9% by weight of dialkylphosphinic acid of the formula (I) and 10 to 0.1% by weight of alkylphosphonic acid of the formula (II).

Especially preferred are mixtures comprising 95 to 99.9% by weight of dialkylphosphinic acid of the formula (I) and 5 to 0.1% by weight of alkylphosphonic acid of the formula (II).

Particularly advantageous mixtures are those comprising 98 to 99.9% by weight of dialkylphosphinic acid of the formula (I) and 2 to 0.1% by weight of alkylphosphonic acid of the formula (II).

Preferably, the dialkylphosphinic acid is diethylphosphinic acid, ethylpropylphosphinic acid, ethylbutylphosphinic acid, ethylpentylphosphinic acid, ethylhexylphosphinic acid, dipropylphosphinic acid, propylbutylphosphinic acid, propylpentylphosphinic acid, propylhexylphosphinic acid, dibutylphosphinic acid, butylpentylphosphinic acid, butylhexylphosphinic acid, dipentylphosphinic acid, pentylhexylphosphinic acid and/or dihexylphosphinic acid; and the alkylphosphonic acid is ethylphosphonic acid, propylphosphonic acid, butylphosphonic acid, pentylphosphonic acid or hexylphosphonic acid.

Especially preferred mixtures are those comprising 98 to 99.9% by weight of diethylphosphinic acid and 0.1 to 2% by weight of ethylphosphonic acid.

The mixture preferably further comprises at least one synergist.

The synergist preferably comprises melem, melam, melon, melamine borate, melamine cyanurate, melamine phosphate, dimelamine phosphate, pentamelamine triphosphate, trimelamine diphosphate, tetrakismelamine triphosphate, hexakismelamine pentaphosphate, melamine diphosphate, melamine tetraphosphate, melamine pyrophosphate, melamine polyphosphate, melam polyphosphate, melem polyphosphate and/or melon polyphosphate; aluminum compounds, magnesium compounds, tin compounds, antimony compounds, zinc compounds, silicon compounds, phosphorus compounds, carbodiimides, phosphazenes, piperazines, piperazine (pyro)phosphates, (poly)isocyanates and/or styrene-acrylic polymers.

The synergist preferably also comprises aluminum hydroxide, halloysites, sapphire products, boehmite, nanoboehmite; magnesium hydroxide; antimony oxides; tin oxides; zinc oxide, zinc hydroxide, zinc oxide hydrate, zinc carbonate, zinc stannate, zinc hydroxystannate, zinc silicate, zinc phosphate, zinc borophosphate, zinc borate and/or zinc molybdate; phosphinic acids and salts thereof, phosphonic acids and salts thereof and/or phosphine oxides; carbonyl-biscaprolactam; nitrogen compounds from the group of oligomeric esters of tris(hydroxyethyl) isocyanurate with aromatic polycarboxylic acids, or benzoguanamine, acetoguanamine, tris(hydroxyethyl) isocyanurate, allantoin, glycoluril, cyanurates, cyanurate-epoxide compounds, urea cyanurate, dicyanamide, guanidine, guanidine phosphate and/or sulfate.

The mixtures preferably comprise 99 to 1% by weight of the mixture of dialkylphosphinic acids of the formula (I) and alkylphosphonic acid of the formula (II) as claimed in at least one of claims 1-3 and 1 to 99% by weight of synergist.

The invention also relates to a process for preparing the mixtures as claimed in at least one of claims 1-3, which comprises reacting a phosphorus source with an alkene and a free-radical initiator and, after addition of a mineral acid and workup, converting it to a mixture of dialkylphosphinic acid according to formula (I) with alkylphosphonic acid of the formula (II).

Preferably, the phosphorus source is sodium hypophosphite, the alkene is ethylene and the mineral acid is sulfuric acid.

Preferably, a solution of sodium hypophosphite is reacted with ethylene to give a salt of diethylphosphinic acid which is then converted by reaction with sulfuric acid, nitric acid, hydrochloric acid and/or acetic acid and subsequent concentration, filtration and distillation to a mixture of diethylphosphinic acid with ethylphosphonic acid.

The reaction temperature is preferably between 50 and 150° C.

The invention also relates to the use of mixtures as claimed in at least one of claims 1-4 as an intermediate for further syntheses, as a binder, as a crosslinker or accelerator in the curing of epoxy resins, polyurethanes and unsaturated polyester resins, as polymer stabilizers, as crop protection compositions, as sequestrants, as a mineral oil additive, as an anticorrosive, in washing and cleaning composition applications and in electronics applications.

The invention additionally relates to the use of mixtures of at least one dialkylphosphinic acid of the formula (I) and at least one alkylphosphonic acid of the formula (II) as claimed in at least one of claims 1-3 as a flame retardant, especially as a flame retardant for clearcoats and intumescent coatings, as a flame retardant for wood and other cellulosic products, as a reactive and/or nonreactive flame retardant for polymers, for production of flame-retardant polymer molding compositions, for production of flame-retardant polymer moldings and/or for rendering polyester and pure and blended cellulose fabrics flame-retardant by impregnation, and as a synergist.

The invention also relates to flame-retardant thermoplastic or thermoset polymer molding compositions and to polymer moldings, films, filaments and fibers comprising 0.5 to 45% by weight of mixtures as claimed in at least one of claims 1-3, 55 to 99.5% by weight of thermoplastic or thermoset polymer or mixtures thereof, 0 to 55% by weight of additives and 0 to 55% by weight of filler or reinforcing materials, where the sum of the components is 100% by weight.

The invention finally also relates to flame-retardant thermoplastic or thermoset polymer molding compositions and to polymer moldings, films, filaments and fibers comprising 1 to 30% by weight of mixtures as claimed in at least one of claims 1-3, 10 to 95% by weight of thermoplastic or thermoset polymer or mixtures thereof, 2 to 30% by weight of additives and 2 to 30% by weight of filler or reinforcing materials, where the sum of the components is 100% by weight.

Preferred two-component mixtures of at least one dialkylphosphinic acid of the formula (I) and at least one alkylphosphonic acid of the formula (II) are composed of
diethylphosphinic acid and ethylphosphonic acid,
diethylphosphinic acid and propylphosphonic acid,
diethylphosphinic acid and butylphosphonic acid,
diethylphosphinic acid and pentylphosphonic acid,
diethylphosphinic acid and hexylphosphonic acid,
ethylpropylphosphinic acid and ethylphosphonic acid,
ethylpropylphosphinic acid and propylphosphonic acid,
ethylpropylphosphinic acid and butylphosphonic acid,
ethylpropylphosphinic acid and pentylphosphonic acid,
ethylpropylphosphinic acid and hexylphosphonic acid,
ethylbutylphosphinic acid and ethylphosphonic acid,
ethylbutylphosphinic acid and propylphosphonic acid,
ethylbutylphosphinic acid and butylphosphonic acid,
ethylbutylphosphinic acid and pentylphosphonic acid,
ethylbutylphosphinic acid and hexylphosphonic acid,
ethylpentylphosphinic acid and ethylphosphonic acid,
ethylpentylphosphinic acid and propylphosphonic acid,
ethylpentylphosphinic acid and butylphosphonic acid,
ethylpentylphosphinic acid and pentylphosphonic acid,
ethylpentylphosphinic acid and hexylphosphonic acid,
ethylhexylphosphinic acid and ethylphosphonic acid,
ethylhexylphosphinic acid and propylphosphonic acid,
ethylhexylphosphinic acid and butylphosphonic acid,
ethylhexylphosphinic acid and pentylphosphonic acid,
ethylhexylphosphinic acid and hexylphosphonic acid,
dipropylphosphinic acid and ethylphosphonic acid,
dipropylphosphinic acid and propylphosphonic acid,
dipropylphosphinic acid and butylphosphonic acid,
dipropylphosphinic acid and pentylphosphonic acid,
dipropylphosphinic acid and hexylphosphonic acid,
propylbutylphosphinic acid and ethylphosphonic acid,
propylbutylphosphinic acid and propylphosphonic acid,
propylbutylphosphinic acid and butylphosphonic acid,
propylbutylphosphinic acid and pentylphosphonic acid,
propylbutylphosphinic acid and hexylphosphonic acid,
propylpentylphosphinic acid and ethylphosphonic acid,
propylpentylphosphinic acid and propylphosphonic acid,
propylpentylphosphinic acid and butylphosphonic acid,
propylpentylphosphinic acid and pentylphosphonic acid,
propylpentylphosphinic acid and hexylphosphonic acid,
propylhexylphosphinic acid and ethylphosphonic acid,
propylhexylphosphinic acid and propylphosphonic acid,
propylhexylphosphinic acid and butylphosphonic acid,
propylhexylphosphinic acid and pentylphosphonic acid,
propylhexylphosphinic acid and hexylphosphonic acid,
dibutylphosphinic acid and ethylphosphonic acid,
dibutylphosphinic acid and propylphosphonic acid,
dibutylphosphinic acid and butylphosphonic acid,
dibutylphosphinic acid and pentylphosphonic acid,
dibutylphosphinic acid and hexylphosphonic acid,
butylpentylphosphinic acid and ethylphosphonic acid,
butylpentylphosphinic acid and propylphosphonic acid,
butylpentylphosphinic acid and butylphosphonic acid,
butylpentylphosphinic acid and pentylphosphonic acid,
butylpentylphosphinic acid and hexylphosphonic acid,
butylhexylphosphinic acid and ethylphosphonic acid,
butylhexylphosphinic acid and propylphosphonic acid,
butylhexylphosphinic acid and butylphosphonic acid, butylhexylphosphinic acid and pentylphosphonic acid,
butylhexylphosphinic acid and hexylphosphonic acid,
dipentylphosphinic acid and ethylphosphonic acid,
dipentylphosphinic acid and propylphosphonic acid,
dipentylphosphinic acid and butylphosphonic acid,
dipentylphosphinic acid and pentylphosphonic acid,
dipentylphosphinic acid and hexylphosphonic acid,
pentylhexylphosphinic acid and ethylphosphonic acid,
pentylhexylphosphinic acid and propylphosphonic acid,
pentylhexylphosphinic acid and butylphosphonic acid,
pentylhexylphosphinic acid and pentylphosphonic acid,
pentylhexylphosphinic acid and hexylphosphonic acid,
dihexylphosphinic acid and ethylphosphonic acid,
dihexylphosphinic acid and propylphosphonic acid,
dihexylphosphinic acid and butylphosphonic acid,
dihexylphosphinic acid and pentylphosphonic acid,
dihexylphosphinic acid and hexylphosphonic acid.

In addition, three-component mixtures are also possible, for instance diethylphosphinic acid and ethylphosphonic acid and butylphosphonic acid,
diethylphosphinic acid and butylethylphosphinic acid and butylphosphonic acid, or four-component mixtures, for example diethylphosphinic acid and octylphosphonic acid and butylethylphosphinic acid and ethylphosphonic acid, and other multicomponent mixtures.

More preferably, $R^1$ and $R^2$ are the same or different and are each ethyl and/or butyl, and $R^3$ is ethyl or butyl.

The invention encompasses especially mixtures consisting of 98 to 99.9% by weight of diethylphosphinic acid and 2 to 0.1% by weight of ethylphosphonic acid.

The synergist is preferably at least one expansion-neutral substance. The expansion-neutral substance prevents the expansion of the polymer or reduces it to extremely low values.

Preferred mixtures with one or more synergists comprise 50 to 99% by weight of mixtures of at least one dialkylphosphinic acid of the formula (I) with at least one alkylphosphonic acid of the formula (II) and 1 to 50% by weight of synergist.

Preference is given to processing the inventive mixture of at least one dialkylphosphinic acid of the formula (I) and at least one alkylphosphonic acid of the formula (II) by mixing it into a polymer system.

The mixing is effected by kneading, dispersing and/or extruding.

Preference is also given to using the inventive mixture of at least one dialkylphosphinic acid of the formula (I) and at least one alkylphosphonic acid of the formula (II) by additive incorporation into a polymer system.

Particular preference is given to using the inventive mixture of at least one dialkylphosphinic acid of the formula (I) and at least one alkylphosphonic acid of the formula (II) by reactive incorporation into a polymer system. Reactive incorporation is characterized by a resulting permanent bond to the polymer extrudates of the polymer system, as a result of which the inventive mixture of at least one dialkylphosphinic acid of the formula (I) and at least one alkylphosphonic acid of the formula (II) cannot be leached out of the polymer.

The inventive mixtures of at least one dialkylphosphinic acid of the formula (I) and at least one alkylphosphonic acid of the formula (II) can be used with further flame retardants and further synergists. The further flame retardants include, for example, phosphorus compounds such as phosphinates, phosphonates, phosphates, phosphonic acids, phosphinic acids, phosphoric acids, phosphines, phosphine oxides, phosphorus oxides and others.

Suitable polymer additives for flame-retardant polymer molding compositions and polymer moldings are UV absorbers, light stabilizers, lubricants, colorants, antistats, nucleating agents, fillers, synergists, reinforcers and others.

The polymer systems preferably originate from the group of the thermoplastic polymers such as polyamide, polyester or polystyrene and/or thermoset polymers.

The thermoset polymers are more preferably epoxy resins.

The thermoset polymers are more preferably epoxy resins which have been cured with phenols and/or dicyandiamide [more generally: phenol derivatives (resols); alcohols and amines], especially phenol derivatives and dicyandiamide.

The thermoset polymers are more preferably epoxy resins which have been cured with phenols and/or dicyandiamide and/or a catalyst.

The catalysts are preferably imidazole compounds.

The epoxy resins are preferably polyepoxide compounds.

The epoxy resins preferably originate from the group of the novolacs and the bisphenol A resins.

Polymers usable in accordance with the invention are thermoset and thermoplastic polymers.

The polymers are preferably polymers of mono- and diolefins, for example polypropylene, polyisobutylene, polybutene-1, poly-4-methylpentene-1, polyisoprene or polybutadiene, and addition polymers of cycloolefins, for example of cyclopentene or norbornene; and also polyethylene (which may optionally be crosslinked), e.g. high-density polyethylene (HDPE), high-density high-molar mass polyethylene (HDPE-HMW), high-density ultrahigh-molar mass polyethylene (HDPE-UHMW), medium-density polyethylene (MDPE), low-density polyethylene (LDPE), linear low-density polyethylene (LLDPE), branched low-density polyethylene (BLDPE), and mixtures thereof.

The polymers are preferably copolymers of mono- and diolefins with one another or with other vinyl monomers, for example ethylene-propylene copolymers, linear low-density polyethylene (LLDPE) and mixtures thereof with low-density polyethylene (LDPE), propylene-butene-1 copolymers, propylene-isobutylene copolymers, ethylene-butene-1 copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and copolymers thereof with carbon monoxide, or ethylene-acrylic acid copolymers and salts thereof (ionomers), and also terpolymers of ethylene with propylene and a diene such as hexadiene, dicyclopentadiene or ethylidenenorbornene; and also mixtures of such copolymers with one another, e.g. polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers and alternating or random polyalkylene/carbon monoxide copolymers and mixtures thereof with other polymers, for example polyamides.

The polymers are preferably hydrocarbon resins (e.g. $C_5$-$C_9$), including hydrogenated modifications thereof (e.g. tackifier resins) and mixtures of polyalkylenes and starch.

The polymers are preferably polystyrene (Polystyrol® 143E (BASF), poly(p-methylstyrene), poly(alpha-methylstyrene).

The polymers are preferably copolymers of styrene or alpha-methylstyrene with dienes or acrylic derivatives, for example styrene-butadiene, styrene-acrylonitrile, styrene-alkyl methacrylate, styrene-butadiene-alkyl acrylate and methacrylate, styrene-maleic anhydride, styrene-acrylonitrile-methyl acrylate; more impact-resistant mixtures of styrene copolymers and another polymer, for example a polyacrylate, a diene polymer or an ethylene-propylene-diene terpolymer; and block copolymers of styrene, for example styrene-butadiene-styrene, styrene-isoprene-styrene, styrene-ethylene/butylene-styrene or styrene-ethylene/propylene-styrene.

The polymers are preferably also graft copolymers of styrene or alpha-methylstyrene, for example styrene onto polybutadiene, styrene onto polybutadiene-styrene or polybutadiene-acrylonitrile copolymers, styrene and acrylonitrile (or methacrylonitrile) onto polybutadiene; styrene, acrylonitrile and methyl methacrylate onto polybutadiene; styrene and maleic anhydride onto polybutadiene; styrene, acrylonitrile and maleic anhydride or maleimide onto polybutadiene; styrene and maleimide onto polybutadiene, styrene and alkyl acrylates or alkyl methacrylates onto polybutadiene, styrene and acrylonitrile onto ethylene-propylene-diene terpolymers, styrene and acrylonitrile onto polyalkyl acrylates or polyalkyl methacrylates, styrene and acrylonitrile onto acrylate-butadiene copolymers, and mixtures thereof, as known, for example, as ABS, MBS, ASA or AES polymers.

The styrene polymers are preferably comparatively coarse-pore foam such as EPS (expanded polystyrene), e.g. Styropor (BASF) and/or foam with relatively fine pores such as XPS (extruded rigid polystyrene foam), e.g. Styrodur® (BASF). Preference is given to polystyrene foams, for example Austrotherm® XPS, Styrofoam® (Dow Chemical), Floormate®, Jackodur®, Lustron®, Roofmate®, Sagex® and Telgopor®.

The polymers are preferably halogenated polymers, for example polychloroprene, chlorine rubber, chlorinated and brominated copolymer of isobutylene-isoprene (halobutyl rubber), chlorinated or chlorosulfonated polyethylene, copolymers of ethylene and chlorinated ethylene, epichlorohydrin homo- and copolymers, especially polymers of halogenated vinyl compounds, for example polyvinyl chloride, polyvinylidene chloride, polyvinyl fluoride, polyvinylidene fluoride; and copolymers thereof, such as vinyl chloride-vinylidene chloride, vinyl chloride-vinyl acetate or vinylidene chloride-vinyl acetate.

The polymers are preferably polymers which derive from alpha,beta-unsaturated acids and derivatives thereof, such as polyacrylates and polymethacrylates, polymethyl methacrylates, polyacrylamides and polyacrylonitriles impact-modified with butyl acrylate, and copolymers of the monomers mentioned with one another or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

The polymers are preferably polymers which derive from unsaturated alcohols and amines or the acyl derivatives or acetals thereof, such as polyvinyl alcohol, polyvinyl acetate, stearate, benzoate or maleate, polyvinyl butyral, polyallyl phthalate, polyallylmelamine; and copolymers thereof with olefins.

The polymers are preferably homo- and copolymers of cyclic ethers, such as polyalkylene glycols, polyethylene oxide, polypropylene oxide or copolymers thereof with bisglycidyl ethers.

The polymers are preferably polyacetals such as polyoxymethylene, and those polyoxymethylenes which contain comonomers, for example ethylene oxide; polyacetals which have been modified with thermoplastic polyurethanes, acrylates or MBS.

The polymers are preferably polyphenylene oxide and sulfides and mixtures thereof with styrene polymers or polyamides.

The polymers are preferably polyurethanes which derive from polyethers, polyesters and polybutadienes having both terminal hydroxyl groups and aliphatic or aromatic polyisocyanates, and the precursors thereof.

The polymers are preferably polyamides and copolyamides which derive from diamines and dicarboxylic acids and/or from aminocarboxylic acids or the corresponding lactams, such as nylon 2/12, nylon 4 (poly-4-aminobutyric acid, Nylon® 4, from DuPont), nylon 4/6 (poly(tetramethyleneadipamide)), Nylon® 4/6, from DuPont), nylon 6 (polycaprolactam, poly-6-aminohexanoic acid, Nylon® 6, from DuPont, Akulon K122, from DSM; Zytel® 7301, from DuPont; Durethan® B 29, from Bayer), nylon 6/16 ((poly (N,N'-hexamethyleneadipamide), Nylon® 6/6, from DuPont, Zytel® 101, from DuPont; Durethan A30, Durethan® AKV, Durethan® AM, from Bayer; Ultramid® A3, Fa BASF), nylon 6/9 (poly(hexamethylenenonanamide), Nylon® 6/9, from DuPont), nylon 6/10 (poly(hexamethylenesebacamide), Nylon® 6/10, from DuPont), nylon 6/12 (poly(hexamethylenedodecanediamide), Nylon®6/12, from DuPont), nylon 6/66 (poly(hexamethyleneadipamide-co-caprolactam), Nylon® 6/66, from DuPont), nylon 7 (poly-7-aminoheptanoic acid, Nylon® 7, from DuPont), nylon 7,7 (polyheptamethylenepimelamide, Nylon® 7,7, from DuPont), nylon 8 (poly-8-aminooctanoic acid, Nylon® 8, from DuPont), nylon 8,8 (polyoctamethylenesuberamide, Nylon® 8,8, from DuPont), nylon 9 (poly-9-aminononanoic acid, Nylon® 9, from DuPont), nylon 9,9 (polynonamethyleneazelamide, Nylon® 9,9, from DuPont), nylon 10 (poly-10-aminodecanoic acid, Nylon® 10, from DuPont), nylon 10,9 (poly(decamethyleneazelamide), Nylon® 10,9, from DuPont), nylon 10,10 (polydecamethylenesebacamide, Nylon® 10,10, from DuPont), nylon 11 (poly-11-aminoundecanoic acid, Nylon® 11, from DuPont), nylon 12 (polylauryllactam, Nylon® 12, from DuPont, Grillamid® L20, from Ems Chemie), aromatic polyamides proceeding from m-xylene, diamine and adipic acid; polyamides prepared from hexamethylenediamine and iso- and/or terephthalic acid (polyhexamethyleneisophthalamide, polyhexamethyleneterephthalamide) and optionally an elastomer as a modifier, e.g. poly-2,4,4-trimethylhexamethyleneterephthalamide or poly-m-phenyleneisophthalamide. Block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. In addition, polyamides or copolyamides modified with EPDM (ethylene-propylene-diene rubber) or ABS (acrylonitrile-butadiene-styrene); and polyamides condensed during processing ("RIM polyamide systems").

The polymers are preferably polyureas, polyimides, polyamidimides, polyetherimides, polyesterimides, polyhydantoins and polybenzimidazoles.

The polymers are preferably polyesters which derive from dicarboxylic acids and dialcohols and/or from hydroxycarboxylic acids or the corresponding lactones, such as polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and block polyether esters which derive from polyethers with hydroxyl end groups; and also polyesters modified with polycarbonates or MBS.

The polymers are preferably polycarbonates and polyester carbonates.

The polymers are preferably polysulfones, polyether sulfones and polyether ketones.

Preferably, the polymers are crosslinked polymers which derive from aldehydes on the one hand, and phenols, urea or melamine on the other hand, such as phenol-formaldehyde, urea-formaldehyde and melamine-formaldehyde resins.

The polymers are preferably drying and nondrying alkyd resins.

The polymers are preferably unsaturated polyester resins which derive from copolyesters of saturated and unsaturated dicarboxylic acids with polyhydric alcohols, and vinyl compounds as crosslinking agents, and also the halogenated, flame-retardant modifications thereof.

The polymers preferably comprise crosslinkable acrylic resins which derive from substituted acrylic esters, for example from epoxy acrylates, urethane acrylates or polyester acrylates.

Preferably, the polymers are alkyd resins, polyester resins and acrylate resins which have been crosslinked with melamine resins, urea resins, isocyanates, isocyanurates, polyisocyanates or epoxy resins.

The polymers are preferably crosslinked epoxy resins which derive from aliphatic, cycloaliphatic, heterocyclic or aromatic glycidyl compounds, for example products of bisphenol A diglycidyl ethers, bisphenol F diglycidyl ethers, which are crosslinked by means of customary hardeners, for example anhydrides or amines, with or without accelerators.

The polymers are preferably mixtures (polyblends) of the above-mentioned polymers, for example PP/EPDM (polypropylene/ethylene-propylene-diene rubber), polyamide/EPDM or ABS (polyamide/ethylene-propylene-diene rubber or acrylonitrile-butadiene-styrene), PVC/EVA (polyvinyl chloride/ethylene-vinyl acetate), PVC/ABS (polyvinyl chloride/acrylonitrile-butadiene-styrene), PVC/MBS (polyvinyl chloride/methacrylate-butadiene-styrene), PC/ABS (polycarbonate/acrylonitrile-butadiene-styrene), PBTP/ABS (polybutylene terephthalate/acrylonitrile-butadiene-styrene), PC/ASA (polycarbonate/acrylic ester-styrene-acrylonitrile), PC/PBT (polycarbonate/polybutylene terephthalate), PVC/CPE (polyvinyl chloride/chlorinated polyethylene), PVC/acrylate (polyvinyl chloride/acrylate, POM/thermoplastic PUR (polyoxymethylene/thermoplastic polyurethane), PC/thermoplastic PUR (polycarbonate/thermoplastic polyurethane), POM/acrylate (polyoxymethylene/acrylate), POM/MBS (polyoxymethylene/methacrylate-butadiene-styrene), PPO/HIPS (polyphenylene oxide/high-impact polystyrene), PPO/PA 6,6 (polyphenylene oxide/nylon 6,6) and copolymers, PA/HDPE (polyamide/high-density polyethylene), PA/PP (polyamide/polyethylene), PA/PPO (polyamide/polyphenylene oxide), PBT/PC/ABS (polybutylene terephthalate/polycarbonate/acrylonitrile-butadiene-styrene) and/or PBT/PET/PC (polybutylene terephthalate/polyethylene terephthalate/polycarbonate).

The polymers may be laser-markable.

The molding produced is preferably of rectangular shape with a regular or irregular base, or of cubic shape, cuboidal shape, cushion shape or prism shape.

Production, processing and testing of flame-retardant polymer molding compositions and flame-retardant polymer moldings The flame-retardant components are mixed with the polymer pellets and any additives and incorporated in a twin-screw extruder (model: Leistritz LSM® 30/34) at temperatures of 230 to 260° C. (PBT-GR) or of 260 to 280° C. (PA 66-GR). The homogenized polymer strand was drawn off, cooled in a water bath and then pelletized.

After sufficient drying, the molding compositions are processed on an injection molding machine (model: Aarburg Allrounder) at melt temperatures of 240 to 270° C. (PBT-GR) or of 260 to 290° C. (PA 66-GR) to give test specimens. The test specimens are tested for flame retardancy and classified using the UL 94 test (Underwriter Laboratories).

Test specimens of each mixture were used to determine the UL 94 fire class (Underwriter Laboratories) on specimens of thickness 1.5 mm.

The UL 94 fire classifications are as follows:

V-0: afterflame time never longer than 10 sec., total of afterflame times for 10 flame applications not more than 50 sec., no flaming drops, no complete consumption of the specimen, afterglow time for specimens never longer than 30 sec. after end of flame application.

V-1: afterflame time never longer than 30 sec. after end of flame application, total of afterflame times for 10 flame applications not more than 250 sec., afterglow time for specimens never longer than 60 sec. after end of flame application, other criteria as for V-0.

V-2: cotton indicator ignited by flaming drops, other criteria as for V-1.

Not classifiable (ncl): does not fulfill fire class V-2.

For some samples examined, the LOI was also measured. The LOI (Limiting Oxygen Index) is determined to ISO 4589. According to ISO 4589, the LOI corresponds to the lowest oxygen concentration in percent by volume which just still supports the combustion of the polymer in a mixture of oxygen and nitrogen. The higher the LOI the greater the nonflammability of the material tested.

| LOI | 23 | flammable |
| LOI | 24-28 | limited flammability |
| LOI | 29-35 | flame-retardant |
| LOI | >36 | particularly flame-retardant |

Chemicals and Abbreviations Used:
Phenol novolac: Bakelite® PF 0790, from Hexion
The invention is illustrated by the examples which follow.

EXAMPLE 1

First of all, according to example 2 of EP-B-1544205, the sodium salt of diethylphosphinic acid is prepared by dissolving 1500 g of sodium hypophosphite monohydrate in 7.5 kg of water and, after heating the reaction mixture to 100° C., introducing ethylene into the reactor until saturation. Under ethylene pressure, a solution of 17 g of sodium peroxodisulfate in 300 g of water was then metered in.

This gives an aqueous reaction solution of the sodium salt of diethylphosphinic acid, which is converted by treatment with nitric acid, concentration, filtration and distillation (1 mbar, 184° C.) to a mixture of diethylphosphinic acid (99.9% by weight) and ethylphosphonic acid (0.1% by weight). (Yield: 92%).

EXAMPLE 2

First of all, as in example 1, an aqueous reaction solution of the sodium salt of diethylphosphinic acid is prepared. This is subsequently converted by treatment with nitric acid, concentration, filtration and distillation (1 mbar, 180-190°

C.) to a mixture of diethylphosphinic acid (98% by weight) and ethylphosphonic acid (2% by weight) (yield: 92%).

EXAMPLE 3

First of all, as in example 1, an aqueous reaction solution of the sodium salt of diethylphosphinic acid is prepared, except using only 95% of the required amount of ethylene. This solution is subsequently converted by treatment with nitric acid, concentration, filtration and distillation (1 mbar, 180-190° C.) to a mixture of diethylphosphinic acid (90% by weight) and ethylphosphonic acid (10% by weight) (yield: 89%).

EXAMPLE 4

First of all, as in example 1, an aqueous reaction solution of the sodium salt of diethylphosphinic acid is prepared, except using only 80% of the required amount of ethylene. This solution is subsequently converted by treatment with nitric acid, concentration, filtration and distillation (1 mbar, 175-195° C.) to a mixture of diethylphosphinic acid (60% by weight) and ethylphosphonic acid (40% by weight) (yield: 93%).

EXAMPLE 5

First of all, as in example 1, an aqueous reaction solution of the sodium salt of diethylphosphinic acid is prepared, except using only 75% of the required amount of ethylene. This solution is subsequently converted by treatment with nitric acid, concentration, filtration and distillation (1 mbar, 175-195° C.) to a mixture of diethylphosphinic acid (50% by weight) and ethylphosphonic acid (50% by weight) (yield: 92%).

Method for Producing Polymer Moldings:

a) Preparation of phosphorus-modified epoxy resin

A 2 l five-neck flask apparatus is initially charged with 1000 g of the epoxy resin (e.g. Beckopox EP 140). It is heated to 110° C. for one hour and volatile components are removed under reduced pressure.

Thereafter, the reaction mixture is inertized with nitrogen and the temperature in the flask is increased to 170° C. 118 g of the mixture of the phosphorus compounds (selected from examples 1 to 5) are added in each case, while stirring under flowing nitrogen, and an exothermic reaction is observed. The resulting resin is yellow in color and free-flowing.

b) Production of epoxy resin specimens 100 parts of the phosphorus-modified epoxy resin are mixed with one corresponding OH equivalent of phenol novolac (hydroxide equivalents 105 g/mol, melting point 85-95° C.) and heated to 150° C. This liquefies the components. The mixture is stirred gradually until a homogeneous mixture has formed and is allowed to cool to 130° C. Then 0.03 part 2-phenylimidazole is added and the mixture is stirred once again for 5-10 min. Thereafter, the mixture is poured warm into a dish and cured at 140° C. for 2 h and at 200° C. for 2 h.

c) Production of epoxy resin laminate 100 parts phosphorus-modified epoxy resin as per b) are added to 63 parts acetone and 27 parts Dowanol® PM, and the appropriate amount of phenol resin is added. The mixture is left to stir for 30 min. and then 2-phenylimidazole is added. Thereafter, the mixture is filtered through a 400 μm sieve in order to remove excess resin particles. Then a woven glass fabric (7628 type, 203 g/m²) is immersed into the solution until complete wetting of the fabric had taken place. The wetted fabric is pulled out of the mixture and excess resin is removed. Thereafter, the wetted fabric is initially cured in stages in a drying cabinet for a brief period at temperatures up to 165° C. and then fully cured in a heated press. The resin content of the cured laminates is 30-50%.

The thermal expansion of the molding produced, a laminate, is determined to ASTM E831-06.

EXAMPLE 6

According to the general method for producing a polymer molding, 100% of a bisphenol A resin is used to produce a laminate, without fractions of the inventive mixture of diethylphosphinic acid and ethylphosphonic acid.

EXAMPLE 7

According to example 3 of EP-B-1544205, 1500 g of sodium hypophosphite monohydrate are dissolved in 7.5 kg of water and, after heating the reaction mixture to 100° C., ethylene is introduced into the reactor until saturation. Under ethylene pressure, a solution of 32 g of ammonium peroxodisulfate in 300 g of water was then metered in. The resulting product was then neutralized with the equivalent amount of sulfuric acid and converted to diethylphosphinic acid and purified appropriately.

According to the general method for producing a polymer molding, a composition composed of 90% by weight of bisphenol A resin with hardener and catalyst and 10% by weight of the aforementioned diethylphosphinic acid is used to produce a molding.

EXAMPLE 8

According to EP-A-2178891, phosphinic acid, by means of catalyst and ethylene, is used to obtain ethylphosphinic acid, which is purified by means of esterification and distillation. Subsequent oxidation with oxygen affords pure ethylphosphonic acid.

According to the general method for producing a polymer molding, a composition composed of 90% by weight of bisphenol A resin with hardener and catalyst and 10% by weight of the resulting ethylphosphonic acid is then used to produce a molding.

EXAMPLE 9

According to the general method for producing a polymer molding, a composition composed of 90% by weight of bisphenol A resin with hardener and catalyst and 10% by weight of the inventive mixture of diethylphosphinic acid and ethylphosphonic acid according to example 1 is used to produce a molding.

EXAMPLE 10

According to the general method for producing a polymer molding, a composition composed of 90% by weight of bisphenol A resin with hardener and catalyst and 10% by weight of the inventive mixture of diethylphosphinic acid and ethylphosphonic acid according to example 2 is used to produce a molding.

EXAMPLE 11

According to the general method for producing a polymer molding, a composition composed of 90% by weight of bisphenol A resin with hardener and catalyst and 10% by weight of the inventive mixture of diethylphosphinic acid and ethylphosphonic acid according to example 3 is used to produce a molding.

EXAMPLE 12

According to the general method for producing a polymer molding, a composition composed of 90% by weight of bisphenol A resin with hardener and catalyst and 10% by weight of the inventive mixture of diethylphosphinic acid and ethylphosphonic acid according to example 4 is used to produce a molding.

EXAMPLE 13

According to the general method for producing a polymer molding, a composition composed of 90% by weight of bisphenol A resin with hardener and catalyst and 10% by weight of the inventive mixture of diethylphosphinic acid and ethylphosphonic acid according to example 5 is used to produce a molding.

The results are reproduced in the following table:

| Composition of polymer system/substance Example | Mixture of dialkylphosphinic acid/alkylphosphonic mixture | | Coefficient of thermal expansion 0°-100° [ppm/° C.] | |
|---|---|---|---|---|---|
| | | acid | Z | X | Y |
| 6 | 100:0 | | 69 | 20 | 7 |
| 7 | 90:10 | 100:0 | 68 | 20 | 7 |
| 8 | 90:10 | 0:100 | 70 | 21 | 7 |
| 9 | 90:10 | 999:0.1 | 66 | 18 | 5 |
| 10 | 90:10 | 98:2 | 63 | 16 | 5 |
| 11 | 90:10 | 90:10 | 60 | 16 | 5 |
| 12 | 90:10 | 60:40 | 58 | 14 | 4 |
| 13 | 90:10 | 50:50 | 58 | 13 | 4 |

Compared to the pure laminate (example 6), there is a decrease in the values for the laminate comprising the inventive mixture of diethylphosphinic acid and ethylphosphonic acid; thermal expansion is thus very low. An increase in the ethylphosphonic acid content brings about a further improvement.

Compared to the prior art (example 6), the inventive mixtures exhibit lower values for the coefficient of thermal expansion, meaning that the inventive products lead to lower expansion of the moldings produced and hence meet the demands on dimensional stability.

The invention claimed is:

1. A mixture of at least one dialkylphosphinic acid of the formula (I)

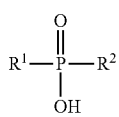

with at least one alkylphosphonic acid of the formula (II)

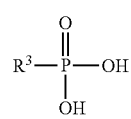

wherein
R$^1$, R$^2$ and R$^3$ are the same or different and are ethyl, n-propyl, n-butyl, isobutyl, tert-butyl, or mixtures thereof, and
at least one synergist, wherein the at least one synergist is melamine cyanurate, melamine polyphosphate, aluminum hydroxide, boehmite, magnesium hydroxide, or zinc borate, and wherein the mixture includes 95 to 99.9% by weight of dialkylphosphinic acid of the formula (I) and 5 to 0.1% by weight of alkylphosphonic acid of the formula (II).

2. The mixture as claimed in claim 1, comprising 98 to 99.9% by weight of dialkylphosphinic acid of the formula (I) and 2 to 0.1% by weight of alkylphosphonic acid of the formula (II).

3. The mixture as claimed in claim 1, wherein the at least one dialkylphosphinic acid is diethylphosphinic acid and the at least one alkylphosphonic acid is ethylphosphonic acid and the mixture comprises 98 to 99.9% by weight of diethylphosphinic acid and 0.1 to 2% by weight of ethylphosphonic acid.

4. A binder, a crosslinker or accelerator in the curing of epoxy resins, polyurethanes and unsaturated polyester resins, a polymer stabilizer, a crop protection composition, a sequestrant, a mineral oil additive, an anticorrosive, a washing composition, a cleaning composition or an electric composition comprising a mixture of at least one dialkylphosphinic acid of the formula (I)

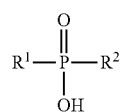

with at least one alkylphosphonic acid of the formula (II)

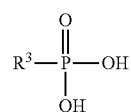

wherein
R$^1$, R$^2$ and R$^3$ are the same or different and are ethyl, n-propyl, n-butyl, isobutyl, tert-butyl, or mixtures thereof, and
at least one synergist, wherein the at least one synergist is melamine cyanurate, melamine polyphosphate, aluminum hydroxide, boehmite, magnesium hydroxide or zinc borate, and wherein the mixture includes 95 to 99.9% by weight of dialkylphosphinic acid of the formula (I) and 5 to 0.1% by weight of alkylphosphonic acid of the formula (II).

* * * * *